United States Patent
Sugo et al.

(10) Patent No.: US 10,301,509 B2
(45) Date of Patent: May 28, 2019

(54) SHEET FOR THERMAL BONDING AND SHEET FOR THERMAL BONDING WITH AFFIXED DICING TAPE

(71) Applicant: NITTO DENKO CORPORATION, Ibaraki-shi, Osaka (JP)

(72) Inventors: Yuki Sugo, Ibaraki (JP); Nao Kamakura, Ibaraki (JP); Tsuyoshi Ishizaka, Ibaraki (JP); Mitsuaki Fusumada, Ibaraki (JP)

(73) Assignee: NITTO DENKO CORPORATION, Ibaraki-shi, Osaka (JP)

( * ) Notice: Subject to any disclaimer, the term of this patent is extended or adjusted under 35 U.S.C. 154(b) by 0 days.

(21) Appl. No.: 15/539,657

(22) PCT Filed: Dec. 11, 2015

(86) PCT No.: PCT/JP2015/084813
§ 371 (c)(1),
(2) Date: Jun. 23, 2017

(87) PCT Pub. No.: WO2016/104188
PCT Pub. Date: Jun. 30, 2016

(65) Prior Publication Data
US 2017/0369744 A1 Dec. 28, 2017

(30) Foreign Application Priority Data

Dec. 24, 2014 (JP) .................................. 2014-260265
Oct. 16, 2015 (JP) .................................. 2015-204211

(51) Int. Cl.
*C08K 3/08* (2006.01)
*C08K 3/22* (2006.01)
(Continued)

(52) U.S. Cl.
CPC . *C09J 5/06* (2013.01); *C09J 7/10* (2018.01); *C09J 7/35* (2018.01); *C09J 9/02* (2013.01);
(Continued)

(58) Field of Classification Search
None
See application file for complete search history.

(56) References Cited

U.S. PATENT DOCUMENTS 4,596,746 A * 6/1986 Morishita ............. B22F 1/0014
419/23
4,708,741 A * 11/1987 Amaya ............... C22C 33/0285
75/255
(Continued)

FOREIGN PATENT DOCUMENTS

EP 2770032 A2 8/2014
JP S48014171 B 5/1973
(Continued)

OTHER PUBLICATIONS

SPB-TE1, Soken, downloaded from URL<https://www.soken-ce.co.jp/en/product/performance_materials/pdf/SPB-TE1.pdf> on Jan. 10, 2018.*
(Continued)

*Primary Examiner* — J. E. Schoenholtz
(74) *Attorney, Agent, or Firm* — Alleman Hall Creasman & Tuttle LLP

(57) ABSTRACT

A sheet for thermal bonding which has a tensile modulus of 10 to 3,000 MPa and contains fine metal particles in an amount in the range of 60-98 wt % and which, when heated from 23° C. to 400° C. in the air at a heating rate of 10° C./min and then examined by energy dispersive X-ray spectrometry, has a carbon concentration of 15 wt % or less.

3 Claims, 1 Drawing Sheet

(51) Int. Cl.

| | |
|---|---|
| *C09J 5/06* | (2006.01) |
| *C09J 7/10* | (2018.01) |
| *C09J 7/35* | (2018.01) |
| *C09J 9/02* | (2006.01) |
| *G01N 1/44* | (2006.01) |
| *C09J 11/04* | (2006.01) |
| *H01L 21/52* | (2006.01) |
| *C09J 133/00* | (2006.01) |
| *C09J 133/08* | (2006.01) |
| *C09J 133/26* | (2006.01) |
| *C09J 169/00* | (2006.01) |
| *C09J 201/08* | (2006.01) |
| *H01L 21/304* | (2006.01) |

(52) U.S. Cl.
CPC ............ *C09J 11/04* (2013.01); *C09J 133/00* (2013.01); *C09J 133/08* (2013.01); *C09J 133/26* (2013.01); *C08K 2003/085* (2013.01); *C08K 2003/0806* (2013.01); *C08K 2003/2248* (2013.01); *C08K 2003/2286* (2013.01); *C08K 2201/001* (2013.01); *C08L 2312/06* (2013.01); *C09J 169/005* (2013.01); *C09J 201/08* (2013.01); *C09J 2201/61* (2013.01); *C09J 2203/326* (2013.01); *C09J 2205/102* (2013.01); *C09J 2433/00* (2013.01); *C09J 2469/00* (2013.01); *G01N 1/44* (2013.01); *H01L 21/3043* (2013.01); *H01L 21/52* (2013.01)

(56) References Cited

U.S. PATENT DOCUMENTS

| | | | | |
|---|---|---|---|---|
| 4,797,251 | A | | 1/1989 | Sakuramoto et al. |
| 4,874,030 | A | * | 10/1989 | Kuphal ............... B22C 7/023 164/34 |
| 5,089,070 | A | * | 2/1992 | McAndrew ............ B32B 18/00 156/89.14 |
| 5,091,346 | A | * | 2/1992 | Inoue .................. B22F 1/0059 501/87 |
| 5,592,686 | A | * | 1/1997 | Third .................. B22F 3/1003 419/2 |
| 5,605,763 | A | | 2/1997 | Yusa et al. |
| 5,667,899 | A | | 9/1997 | Yusa et al. |
| 2004/0221683 | A1 | * | 11/2004 | Shimoda ............... B22F 1/0007 75/252 |
| 2011/0052853 | A1 | | 3/2011 | Sugo et al. |
| 2011/0108971 | A1 | * | 5/2011 | Ewe ....................... H01L 21/56 257/686 |
| 2013/0000811 | A1 | | 1/2013 | Engeldinger et al. |
| 2013/0041093 | A1 | * | 2/2013 | Nakayama ............. C09J 133/00 524/556 |
| 2014/0216644 | A1 | | 8/2014 | Keite-Telgenbuescher |
| 2014/0361445 | A1 | * | 12/2014 | Nashida ................ H01L 25/072 257/782 |
| 2016/0020369 | A1 | * | 1/2016 | Ukawa .................. H01L 33/507 362/311.01 |
| 2016/0151864 | A1 | * | 6/2016 | Rector ...................... B22F 3/10 428/615 |
| 2016/0272488 | A1 | * | 9/2016 | Ogashiwa ......... H01L 23/49827 |
| 2016/0309585 | A1 | * | 10/2016 | Nakamura ........... H05K 1/0296 |

FOREIGN PATENT DOCUMENTS

| | | | | |
|---|---|---|---|---|
| JP | S60230916 | A | | 11/1985 |
| JP | S61276873 | A | | 12/1986 |
| JP | H6145639 | A | | 5/1994 |
| JP | 2005276925 | A | | 10/2005 |
| JP | 2006298954 | A | | 11/2006 |
| JP | 4137827 | B2 | | 8/2008 |
| JP | 2012142368 | A | * | 7/2012 ............ H04L 24/27 |
| JP | 2012142370 | A | | 7/2012 |
| JP | 2013039580 | A | | 2/2013 |
| JP | 2013515113 | A | | 5/2013 |
| JP | 2014111800 | A | | 6/2014 |
| JP | 2014529638 | A | | 11/2014 |
| TW | 201127930 | A1 | | 8/2011 |

OTHER PUBLICATIONS

QPAC-40 Technical Data Sheet, Empower Materials, downloaded from URL<http://empowermaterials.com/wp-content/uploads/2014/11/QPAC-40-Technical-Data-Sheet.pdf> on Jan. 10, 2018.*

Machine translation of JP 2012-42368.*

Machine Translation of JP 2012 142368.*

Calahorra, E., et al. "Thermal Decomposition of Poly(Ethylene Oxide), Poly(Methyl Methacrylate), and Their Mixtures by Thermogravimetric Method." Journal of Polymer Science: Polymer Letters Edition, vol. 23, No. 5, 1985, pp. 257-260., doi:10.1002/pol.1985.130230509.*

The International Bureau of WIPO, International Preliminary Report on Patentability Issued in Japanese Application No. PCT/JP2015/084813, dated Jul. 6, 2017, WIPO, 14 pages.

European Patent Office, Extended European Search Report Issued in European Application No. 15872757.8, dated Nov. 21, 2017, Germany, 8 pages.

Taiwan Intellectual Property Office, Office Action and Search Report Issued in Application No. 104143019, dated Jan. 31, 2019, 11 pages.

* cited by examiner

SHEET FOR THERMAL BONDING AND SHEET FOR THERMAL BONDING WITH AFFIXED DICING TAPE

TECHNICAL FIELD

The present invention relates to a sheet for thermal bonding and a sheet for thermal bonding with an affixed dicing tape.

BACKGROUND ART

In the manufacture of a semiconductor device, a method for bonding a semiconductor element to an adherend such as a metal lead frame (a so-called die bonding method) has been developed from a conventional method for using gold-silicon eutectic bonding to a method for using solder or a resin paste. At the present time, an electrically conductive resin paste may be used.

However, there have been problems in the method for using a resin paste such as a decrease in electrical conductivity due to voids, nonuniformity of the thickness of the resin paste, and contamination of a pad due to protrusion of the resin paste. A polyimide resin-containing film adhesive may be used in place of the resin paste in order to solve these problems (for example, see Patent Document 1).

An acrylic resin-containing film adhesive has also been known. For example, a technique of improving flexibility and reducing heat damage of a lead frame or the like using an acrylic acid copolymer having a glass transition temperature of −10° C. to 50° C. is described in Patent Document 2.

On the other hand, in recent years, a power semiconductor device for controlling and supplying electric power has been remarkably widely used. Since a current always flows in the power semiconductor device, the power semiconductor device has a large heating value. Therefore, an electrically conductive adhesive used for the power semiconductor device desirably has high heat dissipation properties and low electric resistivity.

Low loss and a high-speed operation are required for the power semiconductor device. Conventionally, semiconductors using Si such as IGBT (Insulated Gate Bipolar Transistor) and MOSFET (Metal-Oxide-Semiconductor Field-Effect Transistor) have been used for the power semiconductor device. In recent years, power semiconductor devices using semiconductors such as SiC and GaN have been developed, and are expected to expand from now on.

The semiconductors using SiC and GaN have features such as a large band gap and a high breakdown electrical field to achieve low loss, a high-speed operation, and a high-temperature operation. The high-temperature operation provides a merit in an automobile and a small power converter or the like used in a severe heat environment. In the semiconductor device used in a severe heat environment, a high-temperature operation at about 250° C. is assumed. This causes problems in heat characteristics and reliability in solder and an electrically conductive adhesive as conventional bonding and adhesive materials. Then, conventionally, a sintering metal particle-containing paste material has been proposed (for example, see Patent Document 3). The sintering metal particle-containing paste material contains nanomicro-sized metal particles. These metal particles are melted at a temperature lower than a usual melting point according to a nanosize effect, so that sintering between the particles is achieved. Bonding due to sintering provides high reliability even in an environment of 250° C. and high heat characteristics.

PRIOR ART DOCUMENTS

Patent Documents

Patent Document 1: JP-A-6-145639
Patent Document 2: JP-B2-4137827
Patent Document 3: JP-A-2014-111800
Patent Document 4: JP-A-2013-39580

SUMMARY OF THE INVENTION

Problems to be Solved by the Invention

However, since the sintering metal particle-containing paste material is in a paste state, the sintering metal particle-containing paste material may protrude or creep up onto a chip surface during die attaching of a semiconductor chip. Therefore, a slope or inclination of the material may occur on the chip surface, which may cause a decrease in a yield ratio in the manufacture of a semiconductor device and a variation in performance. Particularly, if a chip is inclined when a high voltage is applied, a bonding distance becomes nonuniform, which causes deterioration in device characteristics. A sheet body for thermal bonding is disclosed in Patent Document 4, but this sheet body for thermal bonding is obtained by pressing a high-viscosity material for thermal bonding into a sheet shape. Concerns about the material for thermal bonding protruding and creeping up onto a chip surface during thermal bonding are not resolved.

The present invention has been made in view of the above-described problem points, and an object thereof is to provide a sheet for thermal bonding preventing the material for thermal bonding from protruding or creeping up onto a chip surface during die attaching, and having high reliability and heat characteristics even in a high-temperature environment, and a sheet for thermal bonding with an affixed dicing tape including the sheet for thermal bonding.

Means for Solving the Problems

The present inventors investigated a sheet for thermal bonding, and a sheet for thermal bonding with an affixed dicing tape including the sheet for thermal bonding to solve the conventional problem points. As a result, it was found that, by adopting the following configuration, a material for thermal bonding is prevented from protruding or creeping up onto a chip surface during die attaching, and high reliability and heat characteristics are obtained even in a high-temperature environment, and the present invention was completed.

That is, a sheet for thermal bonding according to the present invention includes fine metal particles in an amount in a range of 60 to 98% by weight, the sheet for thermal bonding having a carbon concentration of 15% by weight or less obtained by energy dispersive X-ray spectrometry after being heated from 23° C. to 400° C. in the air at a heating rate of 10° C./min, the sheet for thermal bonding having a tensile modulus of 10 to 3,000 MPa obtained by the following tensile test method:

the tensile test method including the steps of:
(1) preparing a sheet for thermal bonding having a thickness of 200 μm, a width of 10 mm, and a length of 40 mm as a test sample;
(2) performing a tensile test under conditions of a distance between chucks of 10 mm, a tensile speed of 50 mm/min, and a temperature of 23° C. to obtain a stress-strain diagrammatic view; and
(3) defining a slope of a straight line portion of the stress-strain diagrammatic view as the tensile modulus.

Since the tensile modulus obtained by the tensile test method is 10 MPa or more, the configuration can prevent a compositional material of the sheet for thermal bonding from protruding or creeping up onto a chip surface during die attaching. Since the tensile modulus is 3,000 MPa or less, a semiconductor wafer can be fixed during dicing, for example.

Since the sheet for thermal bonding includes the fine metal particles in an amount in a range of 60 to 98% by weight, the fine metal particles can be sintered or melted to bond two objects (for example, a semiconductor chip and a lead frame).

Since the sheet for thermal bonding has a carbon concentration of 15% by weight or less obtained by energy dispersive X-ray spectrometry after being heated from 23° C. to 400° C. in the air at a heating rate of 10° C./min, an organic matter is barely present after being heated to 400° C. This provides excellent heat resistance after a thermal bonding step, and high reliability and heat characteristics even in a high-temperature environment.

In this configuration, a peak when differential thermal analysis is performed while being heated from 23° C. to 500° C. in the air at a heating rate of 10° C./min is preferably present at 150° C. to 350° C.

When the peak is present at 150° C. to 350° C., an organic matter (for example, a resin component constituting the sheet for thermal bonding) can be said to be thermally decomposed in this temperature range. This provides excellent heat resistance after the thermal bonding step.

In this configuration, the sheet for thermal bonding preferably includes at least one of an acrylic resin and a polycarbonate resin.

When the sheet for thermal bonding includes at least one of an acrylic resin and a polycarbonate resin, the shape of the sheet is more likely to be maintained before the thermal bonding step. During the thermal bonding step, the organic matter is more likely to be thermally decomposed.

In this configuration, the fine metal particles are preferably made of at least one selected from the group consisting of silver, copper, silver oxide, and copper oxide.

The fine metal particles are made of at least one selected from the group consisting of silver, copper, silver oxide, and copper oxide, which can provide more suitable thermal bonding.

In this configuration, the sheet for thermal bonding has a thickness at 23° C. of 5 to 100 μm.

The sheet for thermal bonding has a thickness at 23° C. of 5 to 100 μm or more, which can further prevent the compositional material of the sheet for thermal bonding from protruding. On the other hand, the sheet for thermal bonding has a thickness at 23° C. of 5 to 100 μm or less, which can further prevent a slope from occurring during thermal bonding.

A sheet for thermal bonding with an affixed dicing tape according to the present invention includes: a dicing tape; and the sheet for thermal bonding laminated on the dicing tape.

According to the sheet for thermal bonding with an affixed dicing tape, the sheet for thermal bonding is integrated with the dicing tape, which can eliminate a step of bonding the sheet for thermal bonding to the dicing tape. The sheet for thermal bonding prevents the compositional material of the sheet for thermal bonding from protruding and from creeping up onto a chip surface during thermal bonding.

The fine metal particles can be sintered or melted to bond two objects (for example, a semiconductor chip and a lead frame).

Since the sheet for thermal bonding has a carbon concentration of 15% by weight or less obtained by energy dispersive X-ray spectrometry after being heated from 23° C. to 400° C. in the air at a heating rate of 10° C./min, an organic matter is barely present after being heated to 400° C. This provides excellent heat resistance after a thermal bonding step, and high reliability and heat characteristics even in a high-temperature environment.

BRIEF DESCRIPTION OF THE DRAWINGS

MODE FOR CARRYING OUT THE INVENTION (Sheet for Thermal Bonding with Affixed Dicing Tape)
A sheet for thermal bonding according to one embodiment of the present invention (hereinafter, referred to as a "sheet for thermal bonding") and a sheet for thermal bonding with an affixed dicing tape will be described below. Examples of the sheet for thermal bonding according to the present embodiment include a sheet for thermal bonding in which a dicing tape is not pasted to the sheet for thermal bonding in a sheet for thermal bonding with an affixed dicing tape to be described below. Therefore, hereinafter, the sheet for thermal bonding with an affixed dicing tape will be described, where the sheet for thermal bonding will be described.

As shown in FIG. 1, a sheet for thermal bonding with an affixed dicing tape 10 has a configuration in which a sheet for thermal bonding 3 is laminated on a dicing tape 11. The dicing tape 11 is configured by laminating a pressure-sensitive adhesive layer 2 on a substrate 1, and the sheet for thermal bonding 3 is provided on the pressure-sensitive adhesive layer 2. The present invention may also have a configuration in which a sheet for thermal bonding 3' is formed only on a work piece pasting portion as in a sheet for the thermal bonding with an affixed dicing tape 12 shown in FIG. 2.

Figure 1:
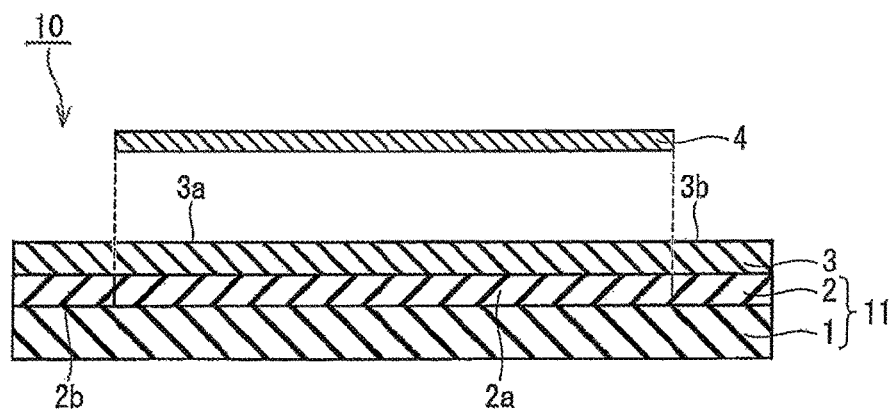
FIG. 1 is a schematic sectional view showing a sheet for thermal bonding with an affixed dicing tape according to one embodiment of the present invention.

(Sheet for Thermal Bonding)
The sheets for thermal bonding 3 and 3' have a tensile modulus of 10 MPa to 3,000 MPa, preferably 12 MPa to 2,900 MPa, and more preferably 15 MPa to 2,500 MPa. The tensile modulus is obtained by the following tensile test method.

Tensile Test Method:
(1) preparing a sheet for thermal bonding (a sheet for thermal bonding for a tensile test) having a thickness of 200 μm, a width of 10 mm, and a length of 40 mm as a test sample;
(2) performing a tensile test under conditions of a distance between chucks of 10 mm, a tensile speed of 50 mm/min, and a temperature of 23° C. to obtain a stress-strain diagrammatic view; and
(3) defining a slope of a straight line portion of the stress-strain diagrammatic view as the tensile modulus.

Since the sheets for thermal bonding 3 and 3' have a tensile modulus of 10 MPa or more obtained by the tensile test method, a compositional material of the sheet for thermal bonding can be prevented from protruding or creeping up onto a chip surface during die attaching. Since the tensile modulus is 3,000 MPa or less, a semiconductor wafer can be fixed during dicing, for example.

The sheets for thermal bonding 3 and 3' include fine metal particles in an amount in a range of 60 to 98% by weight based on the whole sheet for thermal bonding. The content of the fine metal particles is preferably in a range of 65 to 97% by weight, and more preferably in a range of 70 to 95% by weight. Since the sheets for thermal bonding 3 and 3' include the fine metal particles in an amount in a range of 60 to 98% by weight, the fine metal particles can be sintered or melted to bond two objects (for example, a semiconductor chip and a lead frame).

Examples of the fine metal particles include sintering metal particles.

As the sintering metal particles, an aggregate of fine metal particles can be suitably used. Examples of the fine metal particles include fine particles made of a metal. Examples of the metal include gold, silver, copper, silver oxide, and copper oxide. Among these, the metal is preferably at least one selected from the group consisting of silver, copper, silver oxide, and copper oxide. The fine metal particles are made of at least one selected from the group consisting of silver, copper, silver oxide, and copper oxide, which can provide more suitable thermal bonding.

The average particle diameter of the sintering metal particles is preferably 0.0005 μm or more, and more preferably 0.001 μm or more. The average particle diameter may be 0.005 μm or more or 0.01 μm or more. Examples of the lower limit of the average particle diameter include 0.01 μm, 0.05 μm, and 0.1 μm. Other examples thereof include 0.5 μm and 1 μm. On the other hand, the average particle diameter of the sintering metal particles is preferably 30 μm or less, and more preferably 25 μm or less. Examples of the upper limit of the average particle diameter include 20 μm, 15 μm, 10 μm, and 5 μm.

The average particle diameter of the sintering metal particles is measured by the following method. That is, the sintering metal particles are observed by a SEM (scanning electron microscope), to measure an average particle size. During SEM observation, for example, micro-sized sintering metal particles are preferably observed at a magnification of 5,000; submicron-sized sintering metal particles are preferably observed at a magnification of 50,000; and nano-sized sintering metal particles are preferably observed at a magnification of 300,000.

Examples of the shape of the sintering metal particles include a spherical shape, a rod shape, a scale shape, or myriad other shapes without particular limitation.

The sheets for thermal bonding 3 and 3' have a carbon concentration of 15% by weight or less, preferably 12% by weight or less, and more preferably 10% by weight or less. The carbon concentration is obtained by energy dispersive X-ray spectrometry after being heated from 23° C. to 400° C. in the air at a heating rate of 10° C./min. Since the carbon concentration is 15% by weight or less, an organic matter is barely present in the sheets for thermal bonding 3 and 3' heated to 400° C. This provides excellent heat resistance after a thermal bonding step, and high reliability and heat characteristics even in a high-temperature environment.

In the sheets for thermal bonding 3 and 3', a peak when differential thermal analysis is performed while heating from 23° C. to 500° C. in the air at a heating rate of 10° C./min is preferably present at 150 to 350° C., more preferably 170 to 320° C., and still more preferably 180 to 310° C. When the peak is present at 150 to 350° C., an organic matter (for example, a resin component constituting the sheet for thermal bonding) can be said to be thermally decomposed in this temperature range. This provides excellent heat resistance after the thermal bonding step.

The sheets for thermal bonding 3 and 3' preferably contain a thermally-decomposable binder. When the sheets for thermal bonding 3 and 3' contain the thermally-decomposable binder, the shape of the sheet is likely to be maintained before the thermal bonding step. During the thermal bonding step, the sheet for thermal bonding is likely to be thermally decomposed.

Herein, the term "thermally-decomposable binder" refers to a binder which is thermally-decomposable in the thermal bonding step. It is preferable that the thermally-decomposable binder barely remain in the sheet for thermal bonding after the thermal bonding step. Examples of the thermally-decomposable binder include a material having a carbon concentration of 15% by weight or less obtained by energy dispersive X-ray spectrometry after being heated from 23° C. to 400° C. in the air at a heating rate of 10° C./min even if the sheet for thermal bonding contains the material. For example, by adopting a material which is more likely to be thermally decomposed as the thermally-decomposable binder, the material is allowed to barely remain in the sheet for thermal bonding after the thermal bonding step even if the content of the material is comparatively increased.

The thermally-decomposable binder is preferably a solid material at normal temperature (23° C.). When the thermally-decomposable binder is a solid material at normal temperature (23° C.), the sheet for thermal bonding is likely to be formed into a film form at normal temperature, which provides an improvement in handling properties.

Examples of the thermally-decomposable binder include an acrylic resin and a polycarbonate resin.

Examples of the acrylic resin include a polymer (acrylic copolymer) containing, as a component or components, one or more esters of acrylic acid or methacrylic acid having a linear or branched alkyl group having 30 or less carbon atoms, in particular, 4 to 18 carbon atoms in a range in which the acrylic resin can be thermally decomposed in the thermal bonding step. Examples of the alkyl group include a methyl group, an ethyl group, a propyl group, an isopropyl group, an n-butyl group, a t-butyl group, an isobutyl group, an amyl group, an isoamyl group, a hexyl group, a heptyl group, a cyclohexyl group, a 2-ethylhexyl group, an octyl group, an isooctyl group, a nonyl group, an isononyl group, a decyl group, an isodecyl group, an undecyl group, a lauryl group, a tridecyl group, a tetradecyl group, a stearyl group, an octadecyl group, and a dodecyl group.

Other monomers that form the polymer (acrylic copolymer) are not especially limited, and examples thereof include carboxyl group-containing monomers such as acrylic acid, methacrylic acid, carboxyethyl acrylate, carboxypentyl acrylate, itaconic acid, maleic acid, fumaric acid, and crotonic acid, acid anhydride monomers such as maleic anhydride and itaconic anhydride, hydroxyl group-containing monomers such as 2-hydroxyethyl (meth)acrylate, 2-hydroxypropyl (meth)acrylate, 4-hydroxybutyl (meth)acrylate, 6-hydroxyhexyl (meth)acrylate, 8-hydroxyoctyl (meth)acrylate, 10-hydroxydecyl (meth)acrylate, 12-hydroxylauryl (meth)acrylate, and (4-hydroxymethylcyclohexyl)-methylacrylate, sulfonic acid group-containing monomers such as styrene sulfonate, allyl sulfonate, 2-(meth)acrylamide-2-methylpropane sulfonic acid, (meth)acrylamidepropane sulfonic acid, sulfopropyl(meth)acrylate, and (meth)acryloyloxynaphthalene sulfonic acid, and phosphate group-containing monomers such as 2-hydroyethylacryloyl phosphate.

Among the acrylic resins, those more preferably have a weight average molecular weight of 10,000 to 1,000,000, and still more preferably 30,000 to 700,000. When the weight average molecular weight is in the above range, adhesion before the thermal bonding step and thermal decomposition property during the thermal bonding step become excellent. The weight average molecular weight is a value that is measured by GPC (gel permeation chromatography) and calculated with reference to polystyrene.

Among the acrylic resins, an acrylic resin thermally decomposed at 200° C. to 400° C. is preferred.

The polycarbonate resin is not particularly limited as long as the polycarbonate resin can be thermally decomposed in the thermal bonding step. Examples of the polycarbonate resin include aliphatic polycarbonate containing an aliphatic chain without containing an aromatic compound (for example, a benzene ring or the like) between ester carbonate groups (—O—CO—O—) as a main chain, and aromatic polycarbonate containing an aromatic compound between ester carbonate groups (—O—CO—O—) as a main chain. Among these, aliphatic polycarbonate is preferred.

Examples of the aliphatic polycarbonate include polyethylene carbonate and polypropylene carbonate. Among these, polypropylene carbonate is preferred from the viewpoint of solubility in an organic solvent when a varnish for forming a sheet is produced.

Examples of the aromatic polycarbonate include those having a bisphenol A structure as a main chain.

The weight average molecular weight of the polycarbonate resin is suitably in a range of 10,000 to 1,000,000. The weight average molecular weight is a value that is measured by GPC (gel permeation chromatography) and calculated with reference to polystyrene.

The sheets for thermal bonding 3 and 3' may appropriately contain, other than the above-mentioned components, a plasticizer or the like, for example.

The sheets for thermal bonding 3 and 3' can be manufactured by an ordinary method. For example, a varnish that contains each of the above-described components is produced. The varnish is applied onto a substrate separator to form a coating film so as to have a prescribed thickness, and the coating film is then dried to allow the sheets for thermal bonding 3 and 3' to be manufactured.

A solvent that is used in the varnish is not particularly limited. However, an organic solvent or an alcoholic solvent is preferred, which allows each of the above-described components to be dissolved, kneaded, or dispersed, uniformly. Examples of the organic solvent include ketone-based solvents such as dimethylformamide, dimethylacetamide, N-methylpyrrolidone, acetone, methylethylketone, and cyclohexanone; toluene; and xylene. Examples of the alcoholic solvent include ethylene glycol, diethylene glycol, 1,2-propanediol, 1,3-propanediol, 1,2-butanediol, 1,3-butanediol, 1,4-butanediol, 2-butene-1,4-diol, 1,2,6-hexanetriol, glycerin, octanediol, 2-methyl-2,4-pentanediol, and terpineol.

The applying method is not particularly limited. Examples of methods for coating a solvent include a die coater, a gravure coater, a roll coater, a reverse coater, a comma coater, a pipe doctor coater, and screen printing. Among these, a die coater is preferred in terms of high uniformity in an application thickness. The drying condition of the coating film is not particularly limited. For example, drying can be performed at a drying temperature of 70 to 160° C. for a drying time of 1 minute to 5 minutes. Even after the coating film is dried, some solvents may remain in the coating film without the solvents being wholly evaporated.

Polyethylene terephthalate (PET), polyethylene, polypropylene, and a plastic film or a paper or the like whose surface is coated with a peeling agent such as a fluorine based peeling agent and a long chain alkylacrylate based peeling agent can be used as the substrate separator.

A method for mixing each of the above-described components with a mixer and press-molding the obtained mixture to manufacture the sheets for thermal bonding 3 and 3' is also suitable as the method for manufacturing the sheets for thermal bonding 3 and 3'. Examples of the mixer include a planetary mixer.

The thickness of the sheets for thermal bonding 3 and 3' at 23° C. before heating is preferably 5 to 100 µm, and more preferably 10 to 80 µm. The thickness at 23° C. is 5 µm or more, which can further prevent the compositional material of the sheets for thermal bonding 3 and 3' from protruding. On the other hand, the thickness is 100 µm or less, which can further prevent a slope from occurring during thermal bonding.

(Dicing Tape)

A dicing tape 11 has a configuration in which a pressure-sensitive adhesive layer 2 is laminated on a substrate 1.

The base 1 preferably has ultraviolet transmissivity and is a base buoy for strength of the sheets for thermal bonding with an affixed dicing tape 10 and 12. Examples thereof include polyolefin such as low-density polyethylene, straight chain polyethylene, intermediate-density polyethylene, high-density polyethylene, very low-density polyethylene, random copolymer polypropylene, block copolymer polypropylene, homopolypropylene, polybutene, and polymethylpentene; an ethylene-vinylacetate copolymer; an ionomer resin; an ethylene(meth)acrylic acid copolymer; an ethylene (meth)acrylic acid ester (random or alternating) copolymer; an ethylene-butene copolymer; an ethylene-hexene copolymer; polyurethane; polyester such as polyethyleneterephthalate and polyethylenenaphthalate; polycarbonate; polyetheretherketone; polyimide; polyetherimide; polyamide; whole aromatic polyamides; polyphenylsulfide; aramid (paper); glass; glass cloth; a fluorine resin; polyvinyl chloride; polyvinylidene chloride; a cellulose resin; a silicone resin; metal (foil); and paper.

Further, the material of the base 1 includes a polymer such as a cross-linked body of the above resins. The above plastic film may be also used unstreched, or may be used after a monoaxial or a biaxial stretching treatment is performed, depending on necessity. According to resin sheets in which heat shrinkable properties are given by the stretching treatment, etc., the adhesive area of the pressure-sensitive adhesive layer 2 and the sheet for thermal bonding 3, 3' is reduced by thermally shrinking the base 1 after dicing, and the recovery of the semiconductor chips can be facilitated.

A known surface treatment such as a chemical or physical treatment such as a chromate treatment, ozone exposure, flame exposure, high voltage electric exposure, and an ionized ultraviolet treatment, and a coating treatment by an undercoating agent (for example, a tacky substance described later) can be performed on the surface of the base 1 in order to improve adhesiveness, holding properties, etc. with the adjacent layer.

The thickness of the base 1 can be appropriately determined without particular limitation.

The pressure-sensitive adhesive that is used to form the pressure-sensitive adhesive layer 2 is not especially limited. Examples include a general pressure-sensitive adhesive such as an acrylic pressure-sensitive adhesive and a rubber based pressure-sensitive adhesive. As the pressure-sensitive adhesive, an acrylic pressure-sensitive adhesive having an acrylic polymer as a base polymer is preferable from the aspect of a cleaning and washing property of a semiconductor wafer and an electronic component such as a glass which are vulnerable to contamination by ultrapure water and an organic solvent such as alcohol.

Examples of the acrylic polymer include acrylic polymers using, as a monomer component, one or more kinds of (meth)acrylic acid alkyl esters (for example, a straight chain or branched chain alkyl ester having 1 to 30 carbon atoms, and particularly 4 to 18 carbon atoms in the alkyl group such as methylester, ethylester, propylester, isopropylester, butylester, isobutylester, sec-butylester, t-butylester, pentylester, isopentylester, hexylester, heptylester, octylester, 2-ethylhexylester, isooctylester, nonylester, decylester, isodecylester, undecylester, dodecylester, tridecylester, tetradecylester, hexadecylester, octadecylester, and eicosylester) and (meth)acrylic acid cycloalkyl esters (for example, cyclopentylester, cyclohexylester, etc.). The (meth)acrylic acid ester means an acrylic acid ester and/or a methacrylic acid ester, and has very the same meaning as (meth) in the present invention.

The acrylic polymer may optionally contain a unit corresponding to a different monomer component copolymerizable with the above-mentioned alkyl ester of (meth)acrylic acid or cycloalkyl ester thereof in order to improve the cohesive force, heat resistance, or some other property of the polymer. Examples of such a monomer component include carboxyl-containing monomers such as acrylic acid, methacrylic acid, carboxyethyl (meth)acrylate, carboxypentyl (meth)acrylate, itaconic acid, maleic acid, fumaric acid, and crotonic acid; acid anhydride monomers such as maleic anhydride, and itaconic anhydride; hydroxyl-containing monomers such as 2-hydroxyethyl (meth)acrylate, 2-hydroxypropyl (meth)acrylate, 4-hydroxybutyl (meth)acrylate, 6-hydroxyhexyl (meth)acrylate, 8-hydroxyoctyl (meth)acrylate, 10-hydroxydecyl (meth)acrylate, 12-hydroxylauryl (meth) acrylate, and (4-hydroxylmethylcyclohexyl)methyl (meth)acrylate; sulfonic acid group containing monomers such as styrenesulfonic acid, allylsulfonic acid, 2-(meth) acrylamide-2-methylpropanesulfonic acid, (meth)acrylamidepropanesulfonic acid, sulfopropyl (meth)acrylate, and (meth)acryloyloxynaphthalenesulfonic acid; phosphoric acid group containing monomers such as 2-hydroxyethyl-acryloyl phosphate; acrylamide; and acrylonitrile. These copolymerizable monomer components may be used alone or in combination of two or more thereof. The amount of the copolymerizable monomer (s) to be used is preferably 40% or less by weight of all the monomer components.

For crosslinking, the acrylic polymer can also contain multifunctional monomers if necessary as the copolymerizable monomer component. Such multifunctional monomers include hexane diol di(meth)acrylate, (poly)ethylene glycol di(meth)acrylate, (poly)propylene glycol di(meth)acrylate, neopentyl glycol di(meth)acrylate, pentaerythritol di(meth) acrylate, trimethylol propane tri(meth)acrylate, pentaerythritol tri(meth)acrylate, dipentaerythritol hexa(meth)acrylate, epoxy (meth)acrylate, polyester (meth)acrylate, urethane (meth)acrylate etc. These multifunctional monomers can also be used as a mixture of one or more thereof. From the viewpoint of adhesiveness etc., the use amount of the multifunctional monomer is preferably 30 wt % or less based on the whole of the monomer components.

The above acryl-based polymer is obtained by polymerizing a mixture of one or two or more kinds of monomers. The polymerization can be performed by applying an appropriate manner such as a solution polymerization manner, an emulsion polymerization manner, a bulk polymerization manner, or a suspension polymerization manner. From the viewpoint of prevention of contamination of a clean adherend, or the like, the content of a low molecular weight material is preferably prevented. From this viewpoint, the acryl-based polymer preferably has a number average molecular weight of preferably 100,000 or more, more preferably 200,000 to 3,000,000, and particularly preferably 300,000 to 1,000,000.

To increase the number-average molecular weight of the base polymer such as acrylic polymer etc., an external crosslinking agent can be suitably adopted in the pressure-sensitive adhesive. The external crosslinking method is specifically a reaction method that involves adding and reacting a crosslinking agent such as a polyisocyanate compound, epoxy compound, aziridine compound, melamine crosslinking agent, urea resin, anhydrous compound, polyamine, carboxyl group-containing polymer. When the external crosslinking agent is used, the amount of the crosslinking agent to be used is determined suitably depending on balance with the base polymer to be crosslinked and applications thereof as the pressure-sensitive adhesive. In general, the crosslinking agent is compounded preferably about 5 parts by weight or less, and more preferably 0.1 to 5 parts by weight to 100 parts by weight of the base polymer. The conventionally known various additives such as a tackifier and an anti-aging agent may be used as the pressure-sensitive adhesive besides the above-described components as needed.

The pressure-sensitive adhesive layer 2 can be formed with a radiation curing-type pressure-sensitive adhesive. The adhesive strength of the radiation curing-type pressure-sensitive adhesive can be easily reduced by increasing the degree of crosslinking by irradiation with radiation such as ultraviolet rays. A difference in the adhesive strength with the portion 2b can be created by irradiating, with radiation, only the portion 2a that corresponds to the workpiece pasting portion of the pressure-sensitive adhesive layer 2 shown in FIG. 2.

Figure 2:
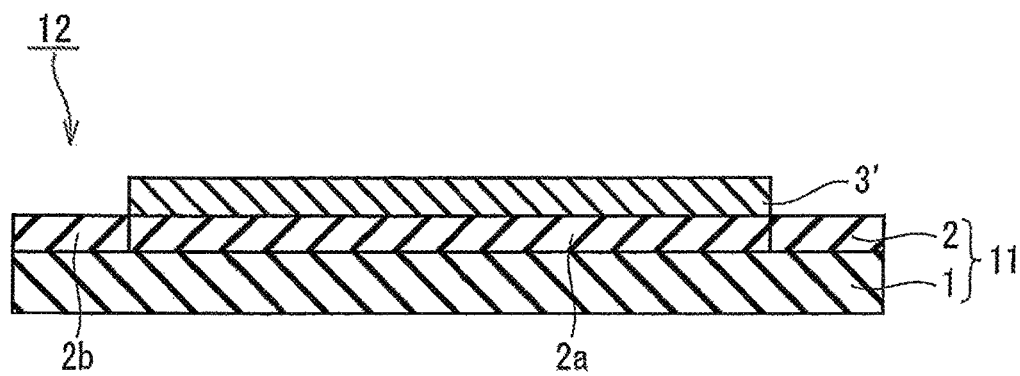
FIG. 2 is a schematic sectional view showing a sheet for thermal bonding with an affixed dicing tape according to another embodiment of the present invention.

The portion 2a where the adhesive strength is markedly reduced can be easily formed by curing the radiation curing-type pressure-sensitive adhesive layer 2 in accordance with the sheet for thermal bonding 3' shown in FIG. 2. Since the sheet for thermal bonding 3' is pasted to the portion 2a that is cured and has decreased adhesive strength, the interface between the portion 2a of the pressure-sensitive adhesive layer 2 and the sheet for thermal bonding 3' has a property of easily peeling during pickup. On the other hand, the portion that is not irradiated with radiation has sufficient adhesive strength, and forms the portion 2b. The pressure-sensitive adhesive layer may be irradiated with radiation after dicing but before pickup.

As described above, in the pressure-sensitive adhesive layer 2 of the sheet for thermal bonding with an affixed dicing tape 10 shown in FIG. 1, the portion 2b that is formed with an uncured radiation curing-type pressure-sensitive adhesive adheres to the sheet for thermal bonding 3, and the holding power can be secured during dicing. Thus, the radiation curable-type pressure-sensitive adhesive can support the sheet for thermal bonding 3 for fixing a chip-shaped workpiece (semiconductor chip or the like) to an adherend such as a substrate with a good balance between adhesion and peeling. In the pressure-sensitive adhesive layer 2 of the sheet 11 for a thermal bonding with an affixed dicing tape shown in FIG. 2, the portion 2b can fix a wafer ring.

For the radiation curing-type pressure-sensitive adhesive, one having a radiation-curable functional group such as a carbon-carbon double bond and showing adherability can be used without particular limitation. Examples of the radiation curing-type pressure-sensitive adhesive include an addition-type radiation-curable pressure-sensitive adhesive obtained by blending a radiation-curable monomer component or an oligomer component with a general pressure-sensitive adhesive such as the above-mentioned acryl-based pressure-sensitive adhesive or rubber-based pressure-sensitive adhesive.

Examples of the radiation-curable monomer component to be compounded include a urethane oligomer, urethane (meth)acrylate, trimethylolpropane tri(meth)acrylate, tetramethylolmethane tetra(meth)acrylate, pentaerythritol tri(meth)acrylate, pentaerythritol tetra(meth)acrylate, dipentaerythritol monohydroxypenta(meth)acrylate, dipentaerythritol hexa(meth)acrylate, and 1,4-butane dioldi(meth)acrylate. Further, the radiation-curable oligomer component includes various types of oligomers such as a urethane based, a polyether based, a polyester based, a polycarbonate based, and a polybutadiene based oligomer, and its molecular weight is appropriately in a range of about 100 to 30,000. The compounding amount of the radiation-curable monomer component and the oligomer component can be appropriately determined to an amount in which the adhesive strength of the pressure-sensitive adhesive layer can be decreased depending on the type of the pressure-sensitive adhesive layer. Generally, it is for example 5 to 500 parts by weight, and preferably about 40 to 150 parts by weight based on 100 parts by weight of the base polymer such as an acrylic polymer constituting the pressure sensitive adhesive.

Further, besides the addition-type radiation-curable pressure-sensitive adhesive described above, the radiation curing-type pressure-sensitive adhesive includes an intrinsic-type radiation-curable pressure-sensitive adhesive using an acrylic polymer having a radical reactive carbon-carbon double bond in the polymer side chain, in the main chain, or at the end of the main chain as the base polymer. The intrinsic-type radiation-curable pressure-sensitive adhesives of an internally provided type are preferable because they do not have to contain the oligomer component, etc. that is a low molecular component, or most of them do not contain, they can form a pressure-sensitive adhesive layer having a stable layer structure without migrating the oligomer component, etc. in the pressure sensitive adhesive over time.

The above-mentioned base polymer, which has a carbon-carbon double bond, may be any polymer that has a carbon-carbon double bond and further has viscosity. As such a base polymer, a polymer having an acrylic polymer as a basic skeleton is preferable. Examples of the basic skeleton of the acrylic polymer include the acrylic polymers exemplified above.

The method for introducing a carbon-carbon double bond into any one of the above-mentioned acrylic polymers is not particularly limited, and may be selected from various methods. The introduction of the carbon-carbon double bond into a side chain of the polymer is easier in molecule design. The method is, for example, a method of copolymerizing a monomer having a functional group with an acrylic polymer, and then causing the resultant to condensation-react or addition-react with a compound having a functional group reactive with the above-mentioned functional group and a carbon-carbon double bond while keeping the radial ray curability of the carbon-carbon double bond.

Examples of the combination of these functional groups include a carboxylic acid group and an epoxy group; a carboxylic acid group and an aziridine group; and a hydroxyl group and an isocyanate group. Of these combinations, the combination of a hydroxyl group and an isocyanate group is preferable from the viewpoint of the easiness of reaction tracing. If the above-mentioned acrylic polymer, which has a carbon-carbon double bond, can be produced by the combination of these functional groups, each of the functional groups may be present on any one of the acrylic polymer and the above-mentioned compound. It is preferable for the above-mentioned preferable combination that the acrylic polymer has the hydroxyl group and the above-mentioned compound has the isocyanate group. Examples of the isocyanate compound in this case, which has a carbon-carbon double bond, include methacryloyl isocyanate, 2-methacryloyloxyethyl isocyanate, and m-isopropenyl-α,α-dimethylbenzyl isocyanate. The used acrylic polymer may be an acrylic polymer copolymerized with any one of the hydroxyl-containing monomers exemplified above, or an ether compound such as 2-hydroxyethyl vinyl ether, 4-hydroxybutyl vinyl ether or diethylene glycol monovinyl ether.

The intrinsic-type radiation-curable pressure-sensitive adhesive may be made only of the above-mentioned base polymer (in particular, the acrylic polymer), which has a carbon-carbon double bond. However, the above-mentioned radiation-curable monomer component or oligomer component may be incorporated into the base polymer to such an extent that properties of the adhesive are not deteriorated. The amount of the radiation-curable oligomer component or the like is usually 30 parts or less by weight, preferably from 0 to 10 parts by weight for 100 parts by weight of the base polymer.

In the case that the radiation-curable pressure-sensitive adhesive is cured with ultraviolet rays or the like, a photopolymerization initiator is incorporated into the adhesive. Examples of the photopolymerization initiator include α-ketol compounds such as 4-(2-hydroxyethoxy)phenyl(2-hydroxy-2-propyl)ketone, α-hydroxy-α,α'-dimethylacetophenone, 2-methyl-2-hydroxypropiophenone, and 1-hydroxycyclohexyl phenyl ketone; acetophenone compounds such as methoxyacetophenone, 2,2-dimethoxy-2-phenylacetophenone, 2,2-diethoxyacetophenone, and 2-methyl-1-[4-(methylthio)-phenyl]-2-morpholinopropane-1-one; benzoin ether compounds such as benzoin ethyl ether, benzoin isopropyl ether, and anisoin methyl ether; ketal compounds such as benzyl dimethyl ketal; aromatic sulfonyl chloride compounds such as 2-naphthalenesulfonyl chloride; optically active oxime compounds such as 1-phenyl-1,1-propanedione-2-(o-ethoxycarbonyl)oxime; benzophenone compounds such as benzophenone, benzoylbenzoic acid, and 3,3'-dimethyl-4-methoxybenzophenone; thioxanthone compound such as thioxanthone, 2-chlorothioxanthone, 2-methylthioxanthone, 2,4-dimethylthioxanthone, isopropylthioxanthone, 2,4-dichlorothioxanthone, 2,4-diethylthioxanthone, and 2,4-diisopropylthioxanthone; camphorquinone; halogenated ketones; acylphosphonoxides; and acylphosphonates. The amount of the photopolymerization initiator to be blended is, for example, from about 0.05 to 20 parts by weight for 100 parts by weight of the acrylic polymer or the like which constitutes the adhesive as a base polymer.

Further, examples of the radiation-curable pressure-sensitive adhesive which is used in the formation of the pressure-sensitive adhesive layer 2 include a rubber pressure-sensitive adhesive or an acryl pressure-sensitive adhesive which contains an addition-polymerizable compound having two or more unsaturated bonds, a photopolymerizable compound such as alkoxysilane having an epoxy group, and a photopolymerization initiator such as a carbonyl compound, an organic sulfur compound, a peroxide, an amine, and an onium salt compound, which are disclosed in JP-A No. 60-196956. Examples of the above addition-polymerizable compound having two or more unsaturated bonds include polyvalent alcohol ester or oligoester of acryl acid or methacrylic acid and an epoxy or a urethane compound.

The radiation curing-type pressure-sensitive adhesive layer 2 can contain a compound that is colored by radiation irradiation as necessary. The compound that is colored by radiation irradiation is contained in the pressure-sensitive adhesive layer 2, so that only a portion irradiated with radiation can be colored. That is, the portion 2a corresponding to the workpiece pasting portion 3a shown in FIG. 1 can be colored. Therefore, whether the pressure-sensitive adhesive layer 2 is irradiated with radiation can be immediately confirmed by visual observation, which enables easy recognition of the workpiece pasting portion 3a, and easy pasting of the workpiece. When a semiconductor chip is detected by a photosensor or the like, the detecting accuracy of the semiconductor chip is increased, which causes no malfunction during the pickup of the semiconductor chip. The compound that is colored by radiation irradiation is colorless or has a pale color before the radiation irradiation. However, the compound is colored by irradiation with radiation. Examples of the compound include a leuco dye. The ratio of use of this compound that is colored by radiation irradiation can be appropriately set.

The thickness of the pressure-sensitive adhesive layer 2 is not particularly limited. However, the thickness is preferably about 1 µm to about 50 µm from the viewpoint of preventing cracking on the cut surface of the chip and maintaining the fixation of the sheets for thermal bonding 3 and 3'. The thickness is preferably 2 µm to 30 µm, and more preferably 5 µm to 25 µm.

The sheets for thermal bonding with an affixed dicing tape 10 and 12 according to the present embodiment are produced, for example, by the following procedure.

First, the base 1 can be formed by a conventionally known film-forming method. The film-forming method includes, for example, a calendar film-forming method, a casting method in an organic solvent, an inflation extrusion method in a closed system, a T-die extrusion method, a co-extrusion method, and a dry lamination method.

Next, a pressure-sensitive adhesive composition solution is applied on the base 1 to form a coated film and the coated film is dried under predetermined conditions (optionally crosslinked with heating) to form the pressure-sensitive adhesive layer 2. Examples of the application method include, but are not limited to, roll coating, screen coating, and gravure coating methods. Drying is conducted under the drying conditions, for example, the drying temperature within a range from 80 to 150° C. and the drying time within a range from 0.5 to 5 minutes. The pressure-sensitive adhesive layer 2 may also be formed by applying a pressure-sensitive adhesive composition on a separator to form a coated film and drying the coated film under the drying conditions. Then, the pressure-sensitive adhesive layer 2 is laminated on the base 1 together with the separator. Thus, the dicing tape 11 is produced.

The sheet for thermal bonding with an affixed dicing tape 10 can be manufactured by an ordinary method. For example, the pressure-sensitive adhesive layer 2 of the dicing tape 11 can be pasted to the sheet for thermal bonding 3 to manufacture the sheet for thermal bonding with an affixed dicing tape 10.

(Method for Manufacturing Semiconductor Device)

A method for manufacturing a semiconductor device according to the present embodiment includes: a step of preparing the sheet for thermal bonding; and a thermal bonding step of thermally bonding a semiconductor chip on an adherend with the sheet for thermal bonding sandwiched therebetween (hereinafter, referred to as a first embodiment).

A method for manufacturing a semiconductor device according to the present embodiment includes: a step of preparing the sheet for thermal bonding with an affixed dicing tape; a pasting step of pasting the sheet for thermal bonding of the sheet for thermal bonding with an affixed dicing tape to a back face of a semiconductor wafer; a dicing step of performing dicing of the semiconductor wafer together with the sheet for thermal bonding, to form a chip-shaped semiconductor chip; a pickup step of performing picking up of the semiconductor chip together with the sheet for thermal bonding from the sheet for thermal bonding with an affixed dicing tape; and a thermal bonding step of thermally bonding the semiconductor chip on an adherend with the sheet for thermal bonding sandwiched therebetween (hereinafter, referred to as a second embodiment).

The method for manufacturing a semiconductor device according to the first embodiment and the method for manufacturing a semiconductor device according to the second embodiment are different from each other in that the method according to the second embodiment uses the sheet for thermal bonding with an affixed dicing tape; by contrast, the method according to the first embodiment uses the sheet for thermal bonding alone. These methods are common in the other points. If a step of pasting the sheet for thermal bonding to the dicing tape after preparing the sheet for thermal bonding is performed in the method for manufacturing a semiconductor device according to the first embodiment, the following steps can be performed in the same manner as in the method for manufacturing a semiconductor device according to the second embodiment. So, hereinafter, the method for manufacturing a semiconductor device according to the second embodiment will be described.

In the method for manufacturing a semiconductor device according to the present embodiment, first, sheets for thermal bonding with an affixed dicing tape 10 and 12 are prepared (preparing step). After a separator that is optionally provided on the sheets for thermal bonding 3, 3' is appropriately peeled off, the sheets for thermal bonding with an affixed dicing tape 10 and 12 are used as follows. Hereinafter, a case where the sheet for thermal bonding with an affixed dicing tape 10 is used will be described as an example with reference to FIG. 3.

First, a semiconductor wafer 4 is press-adhered on a semiconductor wafer pasting portion 3a of the sheet for thermal bonding 3 in the sheet for thermal bonding with an affixed dicing tape 10, and the semiconductor wafer 4 is fixed by adhering and holding (pasting step). The present step is performed while pressing with a pressing means such as a pressing roll. The pasting temperature upon mounting is not particularly limited, and preferably in a range of 23 to 90° C., for example.

Next, the dicing of the semiconductor wafer 4 is performed (dicing step). Accordingly, the semiconductor wafer 4 is cut into a prescribed size and individualized, to manufacture a semiconductor chip 5. The dicing method is not particularly limited, and the method is performed according to a normal method from the circuit face side of the semiconductor wafer 4, for example. The present step can adopt a cutting method called full-cut that forms a slit in the sheet for thermal bonding with an affixed dicing tape 10, or the like, for example. The dicing apparatus used in the present step is not particularly limited, and a conventionally known apparatus can be used. Since the semiconductor wafer 4 is adhered and fixed by the sheet for thermal bonding with an affixed dicing tape 10, chip crack and chip fly can be prevented, and at the same time the damage of the semiconductor wafer 4 can be also prevented.

Next, pickup of the semiconductor chip 5 is performed in order to peel the semiconductor chip 5 that is adhered and fixed to the sheet for thermal bonding with an affixed dicing tape 10 (pickup step). The method for picking up is not particularly limited, and various conventionally known methods can be adopted. Examples thereof include a method for pushing up the individual semiconductor chip 5 from the sheet for thermal bonding with an affixed dicing tape 10 side with a needle and picking up the pushed semiconductor chip 5 with a pick-up apparatus.

As pickup conditions, a needle push-up speed is preferably set to 5 to 100 mm/second, and more preferably 5 to 10 mm/second from the viewpoint of preventing chipping.

When the pressure-sensitive adhesive layer 2 is an ultraviolet-ray curing-type layer, pickup is performed after irradiating the pressure-sensitive adhesive layer 2 with ultraviolet rays. Accordingly, the adhesive strength of the pressure-sensitive adhesive layer 2 to the sheet for thermal bonding 3 is decreased, and the peeling of the semiconductor chip 5 becomes easy. As a result, picking up becomes possible without damaging the semiconductor chip 5. The conditions such as irradiation intensity and irradiation time during irradiation with ultraviolet rays are not particularly limited, and may be appropriately set as necessary. A known light source can be used as a light source used for irradiation with ultraviolet rays. When a pressure-sensitive adhesive layer is previously cured by irradiation with ultraviolet rays, and the cured pressure-sensitive adhesive layer is pasted to a sheet for thermal bonding, the irradiation with ultraviolet rays is unnecessary.

Next, the semiconductor chip 5 that is picked up is die-attached (thermally bonded) to an adherend 6 with the sheet for thermal bonding 3 sandwiched therebetween (thermal bonding step). Examples of the adherend 6 include a lead frame, a TAB film, a substrate, and a semiconductor chip that is separately produced. The adherend 6 may be a deformation type adherend that can be easily deformed or a non-deformation type adherend that is difficult to be deformed (semiconductor wafer or the like), for example.

Examples of the lead frame include a metal lead frame such as a Cu lead frame or a 42 Alloy lead frame. As the substrate, a conventionally known substrate can be used. Examples thereof include an organic substrate made of glass epoxy resin, BT (bismaleimide-triazine), or polyimide. Among these, the metal lead frame can be integrated with the fine metal particles by thermal bonding. Examples of the substrate include an insulating circuit board in which a copper circuit board is laminated on an insulating substrate such as a ceramic plate. By using the insulating circuit board, a power semiconductor device for controlling and supplying electric power can be manufactured, for example.

In the thermal bonding step, the fine metal particles are sintered by heating, and the thermally-decomposable binder is thermally decomposed as necessary. A heating temperature is preferably 180 to 400° C., more preferably 190 to 370° C., and still more preferably 200 to 350° C. A heating time is preferably 0.3 to 300 minutes, more preferably 0.5 to 240 minutes, and still more preferably 1 to 180 minutes. Thermal bonding may be performed under a pressurized condition. The pressurized condition is preferably in a range of 1 to 500 kg/cm$^2$, and more preferably in a range of 5 to 400 kg/cm$^2$. Thermal bonding under pressure can be executed by an apparatus that can simultaneously perform heating and pressurizing, such as a flip chip bonder, for example. A parallel plate press may also be used.

Since the tensile modulus obtained by the tensile test method is 10 MPa or more, the sheet for thermal bonding 3 can prevent the compositional material of the sheet for thermal bonding 3 from protruding or creeping up on the surface of the semiconductor chip 5 during die attaching (during thermal bonding).

Since the sheet for thermal bonding 3 includes the fine metal particles in an amount in a range of 60 to 98% by weight, the fine metal particles can be sintered or melted to bond the semiconductor chip 5 to the adherend 6 (for example, lead frame).

Since the sheet for thermal bonding 3 has a carbon concentration of 15% by weight or less obtained by energy dispersive X-ray spectrometry after being heated from 23° C. to 400° C. in the air at a heating rate of 10° C./min, the organic matter is barely present after the thermal bonding step. This provides excellent heat resistance after the thermal bonding step, and high reliability and heat characteristics even in the high-temperature environment.

Figure 3:
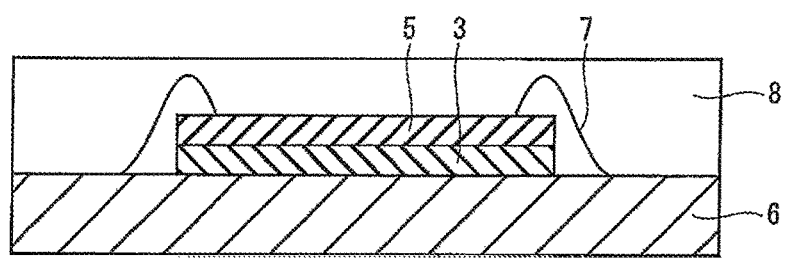
FIG. 3 is a schematic sectional view for illustrating a method for manufacturing a semiconductor device according to the present embodiment.

Next, as necessary, as shown in FIG. 3, the tip of a terminal part (inner lead) of the adherend 6 is electrically connected with an electrode pad (not shown) on the semiconductor chip 5 with a bonding wire 7 (wire bonding step). As the bonding wire 7, for example, a gold wire, an aluminum wire, or a copper wire or the like is used. The temperature when the wire bonding is performed is from 23 to 300° C., and preferably from 23 to 250° C. The temperature may be from 80 to 250° C., or from 80 to 220° C. The heating time is from several seconds to several minutes. The connection of the wires is performed using a combination of vibration energy based on ultrasonic waves with compression energy based on the application of pressure in a state where the wires are heated to a temperature in the above-mentioned range.

Next, as necessary, as shown in FIG. 3, the semiconductor chip 5 is sealed with a sealing resin 8 (sealing step). This step is performed for protecting the semiconductor chip 5 that is loaded on the adherend 6 and the bonding wire 7. This step can be performed by molding a resin for sealing with a mold. As the sealing resin 8, an epoxy-based resin is used, for example. The resin sealing is usually performed at a heating temperature of 175° C. for 60 to 90 seconds, but the present invention is not limited thereto. For example, curing can be performed at 165 to 185° C. for several minutes.

Therefore, the sealing resin 8 is cured. In this sealing step, a method for embedding a semiconductor chip 5 in a sheet shaped sealing sheet (for example, see JP-A-2013-7028) can also be adopted. In addition to the method for molding a sealing resin with a mold, a gel sealing method for casting a silicone gel into a case type container may be used.

Next, heating is performed as necessary, to completely cure the sealing resin 8 that is insufficiently cured in the sealing step (post curing step). The heating temperature in this step differs depending on the type of the sealing resin. However, the heating temperature is in a range of 165 to 185° C., for example, and the heating time is in a range of about 0.5 to about 8 hours.

The sheet for thermal bonding of the present invention and the sheet for thermal bonding with an affixed dicing tape can be suitably used when laminating a plurality of semiconductor chips to carry out three-dimensional mounting. At this time, a sheet for thermal bonding and a spacer may be laminated between the semiconductor chips, or only a sheet for thermal bonding may be laminated between semiconductor chips without laminating a spacer. The mode of mounting can be appropriately changed according to the manufacturing condition and the use, or the like.

The sheet for thermal bonding of the present invention and the sheet for thermal bonding with an affixed dicing tape are not limited to the uses illustrated above, and can be used for thermally bonding two objects.

EXAMPLES

Hereinafter, the present invention will be described in detail by way of examples. However, the present invention is not limited to the examples below.

The components that were used in the examples will be described.

Acrylic resin A: SPB-TE1 manufactured by Soken Chemical & Engineering Co., Ltd. (molecular weight: 40,000)

Acrylic resin B: IB-27 manufactured by Soken Chemical & Engineering Co., Ltd. (molecular weight: 370,000)

Polypropylene carbonate resin: QPAC40 manufactured by Empower Materials Inc. (molecular weight: 200,000)

Ethyl cellulose A: ETHOCEL STD100 manufactured by Nisshin Kasei Co., Ltd.

Fine metal particles A: SPH02J manufactured by Mitsui Mining and Smelting Co., Ltd. (aggregate of fine silver particles, average particle diameter of aggregate: 1.8 μm, infinite shape)

Fine metal particles-containing paste A: ANP-1 manufactured by Applied Nanoparticle Laboratory Corporation (paste in which nano-sized fine silver particles were dispersed)

Organic solvent A: methyl ethyl ketone (MEK)
Alcoholic solvent A: Terpineol
[Production of Sheet for Thermal Bonding]

According to the ratio of blending of compounds described in Table 1, each component and solvent described in Table 1 were placed in a stirring pot of a hybrid mixer (HM-500 manufactured by KEYENCE CORPORATION), and they were stirred and mixed in a stirring mode for 3 minutes. The obtained varnish was applied onto a released-treated film (MRA50 manufactured by Mitsubishi Plastics, Inc.), followed by drying (at 110° C. for 2 minutes). Thereby, sheets for thermal bonding each having a thickness of 50 μm according to Examples and Comparative Examples were obtained. Comparative Example 1 could not provide a uniform sheet.

[Measurement of Tensile Modulus]

(1) First, the sheets for thermal bonding obtained in Examples and Comparative Examples were laminated so that the thickness of the laminated body was set to 200 μm. Next, the laminated body was cut in a width of 10 mm and a length of 30 mm.

(2) Next, a tensile test was performed under conditions of a distance between chucks of 10 mm, a tensile speed of 50 mm/min, and a temperature of 23° C. Autograph AGS-J manufactured by Shimadzu Corporation was used for the tensile test.

(3) Next, a slope of a tangent line at stresses of 0.5 N and 1 N of an obtained stress-strain diagrammatic view was defined as a tensile modulus.

b. The results are shown in Table 1.

[Measurement of Carbon Concentration after Heating]

The sheets for thermal bonding obtained in Examples and Comparative Examples were heated from 23° C. to 400° C. in the air at a heating rate of 10° C./min. After the sheets for thermal bonding were heated to 400° C., the sheets for thermal bonding were allowed to stand for cooling to normal temperature. An oven was used for heating. Next, the heated sample (normal temperature) was subjected to elemental analysis (quantitative analysis) according to EDX (energy dispersive X-ray spectrometry) to measure a carbon concentration (% by weight). Product name: EDAX Model PV77-50780ME manufactured by AMETEK Co., Ltd. was used for measurement. The results are shown in Table 1.

[Peak Temperature Obtained by Differential Thermal Analysis]

The sheets for thermal bonding obtained in Examples and Comparative Examples were subjected to differential thermal analysis from 23° C. to 500° C. in the air at a heating rate of 10° C./min. A TG-DTA simultaneous analyzer (simultaneous thermogravimetric and differential thermal analyzer), more specifically, product name: Thermo Plus TG8210 manufactured by Rigaku Corporation was used for measurement. Next, the temperature of the peak value was read from the obtained graph. The results are shown in Table 1.

TABLE 1

| | | | Example 1 | Example 2 | Example 3 | Example 4 | Example 5 | Comparative Example 1 | Comparative Example 2 |
|---|---|---|---|---|---|---|---|---|---|
| Blending (part by weight) | Acrylic resin A | SPB-TE1 | — | — | 3.2 | 1.1 | — | — | — |
| | Acrylic resin B | IB-27 | 3.5 | 3.2 | — | — | — | — | — |
| | Polypropylene carbonate resin | QPAC40 | — | — | — | — | 0.8 | — | — |
| | Ethyl cellulose A | ETHOCEL STD100 | — | — | — | — | — | — | 3.5 |
| | Fine metal particles A | SPH02J | 54.4 | — | — | — | — | 57.9 | 54.4 |
| | Fine metal particles-containing paste A | ANP-1 | — | 52.7 | 52.1 | 54.9 | 73.5 | — | — |

TABLE 1-continued

|  |  | Example 1 | Example 2 | Example 3 | Example 4 | Example 5 | Comparative Example 1 | Comparative Example 2 |
|---|---|---|---|---|---|---|---|---|
|  | Organic solvent A | Methyl ethyl ketone | 30.5 | 44.1 | 44.7 | 44.00 | 25.7 | 30.5 | 30.5 |
|  | Alcoholic solvent A | Terpineol | 11.6 | — | — | — | — | 11.60 | 11.60 |
|  | Total (part by weight) |  | 100 | 100 | 100 | 100 | 100 | 100 | 100 |
|  | Thickness of sheet (μm) |  | 50 | 50 | 50 | 50 | 50 | — | 50 |
|  | Content of fine metal particles in sheet (% by weight) |  | 78.4 | 75.5 | 85.6 | 89.0 | 95.0 | — | 78.4 |
| Evaluation | Tensile modulus (MPa) |  | 111 | 47.5 | 138 | 83.1 | 270 | — | 120 |
|  | Carbon concentration after heating (% by weight) |  | 9 | 7 | 10 | 5 | 1 | — | 20 |
|  | Peak temperature obtained by differential thermal analysis (° C.) |  | 230 | 230 | 265 | 265 | 310 | — | 470 |

DESCRIPTION OF REFERENCE CHARACTERS

1: substrate
2: pressure-sensitive adhesive layer
3': sheet for thermal bonding
4: semiconductor wafer
5: semiconductor chip
6: adherend
7: bonding wire
8: sealing resin
10, 12: sheet for thermal bonding with affixed dicing tape
11: dicing tape

The invention claimed is:

1. A sheet for thermal bonding comprising fine metal particles in an amount in a range of 70 to 98% by weight,
the sheet for thermal bonding having a carbon concentration of 15% by weight or less obtained by energy dispersive X-ray spectrometry after being heated from 23° C. to 400° C. in the air at a heating rate of 10° C./min,
the sheet for thermal bonding having a tensile modulus of 10 to 3,000 MPa obtained by the following tensile test method:
the tensile test method comprising the steps of:
(1) preparing a sheet for thermal bonding having a thickness of 200 μm, a width of 10 mm, and a length of 40 mm as a test sample;
(2) performing a tensile test under conditions of a distance between chucks of 10 mm, a tensile speed of 50 mm/min, and a temperature of 23° C. to obtain a stress-strain diagrammatic view; and
(3) defining a slope of a straight line portion of the stress-strain diagrammatic view as the tensile modulus, wherein
the sheet for thermal bonding includes at least one thermally-decomposable binder selected from the group consisting of an acrylic resin and a polycarbonate resin,
the fine metal particles, which are an aggregate of fine metal particles, are made of at least one selected from the group consisting of silver, copper, silver oxide, and copper oxide, and
a peak when differential thermal analysis is performed while heating from 23° C. to 500° C. in the air at a heating rate of 10° C./min is present at 150° C. to 350° C.

2. The sheet for thermal bonding according to claim 1, wherein the sheet for thermal bonding has a thickness at 23° C. of 5 to 100 μm.

3. A sheet for thermal bonding with an affixed dicing tape comprising:
a dicing tape; and
the sheet for thermal bonding according to claim 1 laminated on the dicing tape.

* * * * *